United States Patent
Astle

(10) Patent No.: US 9,150,983 B1
(45) Date of Patent: Oct. 6, 2015

(54) AUTOMATED DRIED BLOOD SPOT SYSTEM AND METHOD

(76) Inventor: Thomas W. Astle, Orange, CT (US)

(*) Notice: Subject to any disclaimer, the term of this patent is extended or adjusted under 35 U.S.C. 154(b) by 732 days.

(21) Appl. No.: 13/462,025

(22) Filed: May 2, 2012

(51) Int. Cl.
*G01N 1/00* (2006.01)
*G01N 1/18* (2006.01)
*C40B 60/14* (2006.01)

(52) U.S. Cl.
CPC ...................... *C40B 60/14* (2013.01)

(58) Field of Classification Search
CPC .... G01N 1/403; G01N 1/34; G01N 2030/009
USPC ......................................... 436/174, 177, 178
See application file for complete search history.

(56) References Cited

U.S. PATENT DOCUMENTS

| | | | |
|---|---|---|---|
| 4,668,472 A | 5/1987 | Sakamoto et al. | |
| 5,139,031 A | 8/1992 | Guirguis | |
| 5,139,685 A | 8/1992 | de Castro et al. | |
| 5,597,532 A | 1/1997 | Connolly | |
| 6,818,180 B2 | 11/2004 | Douglas et al. | |
| 8,025,850 B2 | 9/2011 | Chan | |
| 8,586,382 B2 * | 11/2013 | Gijlers et al. | 436/178 |

* cited by examiner

*Primary Examiner* — Chikaodili E Anyikire
(74) *Attorney, Agent, or Firm* — DeLio, Peterson & Curcio LLC; Kelly M. Nowak

(57) ABSTRACT

Apparatus, methods and systems having first and second imaging stations for processing a specimen collection slide having a specimen adsorbed there-through. The first imaging station having a first camera adjacent a first surface of the sample slide and a first lighting assembly directed at an opposite surface of the slide to capture the first surface image, while the second imaging station has a second camera adjacent the second surface and a second lighting assembly directed at the first slide surface to capture a second surface image. A computing device having sets of instructions receives and analyzes the imaging data from the first and second imaging stations, and identifies a location of the absorbed specimen for removal. A punch removes this identified location of the absorbed specimen on the sample slide.

20 Claims, 13 Drawing Sheets

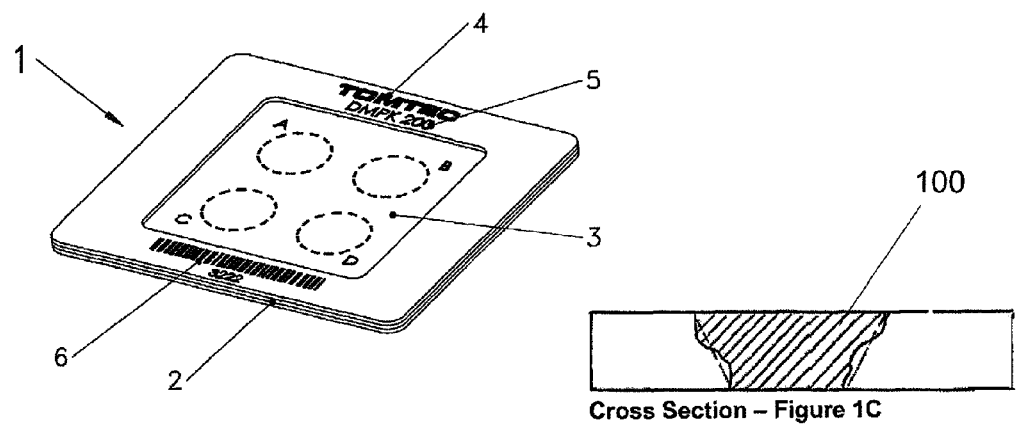
FIG. 1A
FIG. 1C
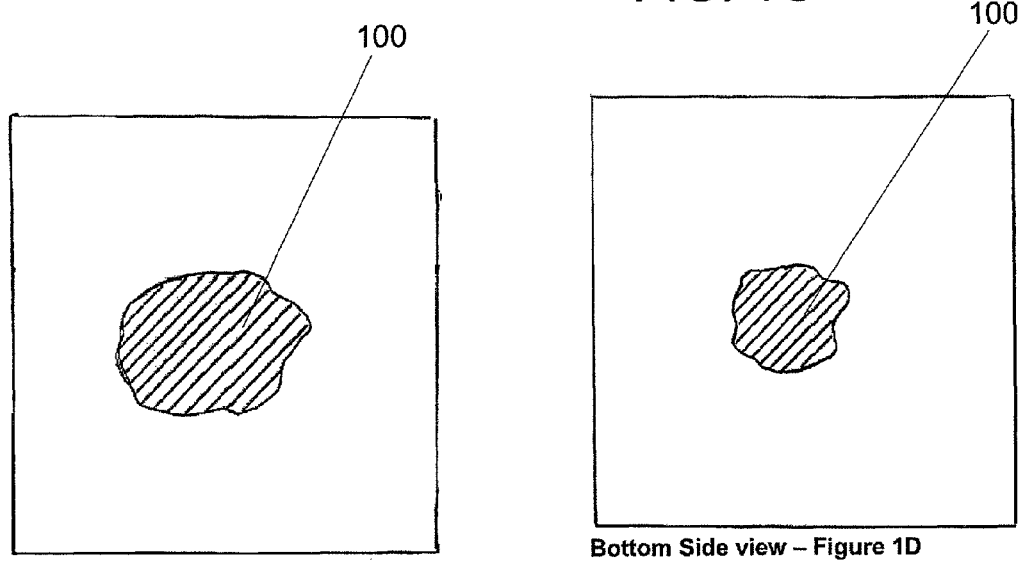
FIG. 1B
FIG. 1D

Scanned DBS Card Images

Front Side                              Back Side

Calculated Volumes of spots in mm³

| DMPK 200 | | | | | | |
|---|---|---|---|---|---|---|
| Hematocrit | Pipettor Volume | | | Aqua Cap Volume | | |
| Level | 15uL | 25uL | 40uL | 15uL | 25uL | 40uL |
| 25% | 19.36 | 32.47 | 52.22 | 21.75 | 34.68 | 53.56 |
| 35% | 19.07 | 32.66 | 51.39 | 21.10 | 33.40 | 52.15 |
| 45% | 18.58 | 29.79 | 47.32 | 19.58 | 31.78 | 49.45 |
| 55% | 18.01 | 29.76 | 45.87 | 19.37 | 31.31 | 47.60 |
| 65% | 17.51 | 27.47 | 41.50 | 18.57 | 29.35 | 43.82 |
| 75% | 15.59 | 23.95 | 35.82 | 16.70 | 27.01 | 37.76 |

| DMPK 300 | | | | | | |
|---|---|---|---|---|---|---|
| Hematocrit | Pipettor Volume | | | Aqua Cap Volume | | |
| Level | 15uL | 25uL | 40uL | 15uL | 25uL | 40uL |
| 25% | 25.65 | 41.22 | 65.23 | 26.78 | 42.06 | 65.56 |
| 35% | 23.25 | 37.93 | 58.47 | 24.67 | 38.54 | 60.75 |
| 45% | 19.11 | 30.98 | 48.47 | 20.33 | 32.72 | 50.40 |
| 55% | 19.16 | 29.67 | 45.37 | 20.09 | 32.13 | 47.92 |
| 65% | 17.27 | 28.10 | 43.35 | 19.21 | 30.44 | 46.10 |
| 75% | 16.78 | 25.95 | 40.68 | 18.13 | 29.78 | 43.49 |

| DMPK 400 | | | | | | |
|---|---|---|---|---|---|---|
| Hematocrit | Pipettor Volume | | | Aqua Cap Volume | | |
| Level | 15uL | 25uL | 40uL | 15uL | 25uL | 40uL |
| 25% | 24.74 | 39.41 | 61.67 | 25.11 | 40.61 | 63.07 |
| 35% | 22.20 | 35.87 | 56.26 | 23.00 | 36.51 | 57.98 |
| 45% | 18.79 | 30.93 | 48.77 | 20.22 | 32.74 | 50.53 |
| 55% | 18.84 | 30.30 | 46.29 | 19.99 | 31.71 | 48.13 |
| 65% | 17.06 | 28.33 | 43.53 | 18.93 | 30.38 | 46.47 |
| 75% | 17.63 | 26.92 | 41.52 | 18.11 | 30.07 | 44.27 |

FIG. 14

AUTOMATED DRIED BLOOD SPOT SYSTEM AND METHOD

BACKGROUND OF THE INVENTION

1. Field of the Invention

The present invention is directed to dried blood spots, and in particular, to systems and methods of obtaining and sampling dried blood spots for the analysis thereof.

2. Description of Related Art

In 1963 Guthrie developed a method for collecting blood samples on absorbent filtration media. The blood samples were dried and transported to the laboratory for analysis. Today, dried blood spots (DBS) are used for mandatory newborn screening programs in the U.S. and in many other nations worldwide. DBS methods have also become common in other medical and forensic applications.

With the advancement of analyte detection methods, primarily liquid chromatography combined with mass spectroscopy (LC-MS or LC-MS/MS), interest has been expanded for the use of DBS for preclinical and clinical applications in lieu of plasma. The small blood volumes required, and the lower transportation and storage costs, are the driving factors. For preclinical applications, there is a significant reduction in the number of animals that are sacrificed, contributing to the ethics of DBS. Dried blood spots are also stable for an extended period of time, often measured in years if the DBS is kept dry. This eliminates the cold storage and shipping requirement needs of plasma, which will drastically reduce costs.

A change from plasma to DBS creates many new challenges to meet the requirements of public health. For the last two years, extensive method development for DBS has occurred in the Bioanalytical market to meet the requirements that are being defined by the U.S. Food and Drug Administration (hereinafter "FDA") for meeting public health safety standards. The FDA, as the guardian of public health, will accept DBS studies only after they have met or exceeded predefined health standards that have been established for plasma. The present invention addresses such needs.

SUMMARY OF THE INVENTION

Bearing in mind the problems and deficiencies of the prior art, it is therefore an object of the present invention to provide systems that easily, efficiently and accurately obtain a sample from a filtration media slide for analysis.

It is another object of the present invention to provide methods for easily, efficiently and accurately obtaining samplings or portions of dried specimens stored on a filtration media slide for analysis.

Another object of the present invention is to provide systems and methods for easily, efficiently and accurately obtaining dried blood spots from media slides for analysis.

A further object of the invention is to provide systems and methods for ethically obtaining specimen samples thereby reducing animal sacrifice.

It is yet another object of the present invention to provide systems and methods of obtaining specimen samples (e.g., dried blood spot samples) that are cost effective and allow for faster processing times.

Still another object of the invention is to provide systems and methods that identify and obtain a best punch location within a dried specimen spot from which to take a sampling there-from.

Still other objects and advantages of the invention will in part be obvious and will in part be apparent from the specification.

The above and other objects, which will be apparent to those skilled in the art, are achieved in the present invention which is directed to apparatus for processing a specimen collection slide. The apparatus includes a slide transport component for receiving and holding a sample slide containing an absorbed specimen, and first and second imaging stations. The first imaging station has a first lighting assembly and a first camera that images a first surface of the sample slide. The first camera is adjacent to and directed at the first surface of the sample slide and the first lighting assembly is directed at an opposite second surface of the sample slide for capturing the first surface image. The second imaging station has a second lighting assembly and a second camera that images the second surface of the sample slide. The second camera is adjacent to and directed at the second surface of the sample slide and the second lighting assembly is directed at the first surface of the sample slide for capturing the second surface image. The apparatus also includes a computing device and a punch. The computing device receives imaging data from the first and second imaging stations and includes a set of instructions that analyze the imaging data and identify a location of the absorbed specimen for removal. The punch removes this identified location of the absorbed specimen on the sample slide.

In one or more embodiments, the first surface may be the front side of the sample slide while the second surface may be the backside of the sample slide. In other embodiments, the first surface may be the backside of the sample slide while the second surface may be the front side of the sample slide. The sample slide may be a dried blood spot specimen slide.

The invention is also directed to methods of processing a specimen collection slide that include providing a sample slide containing a specimen absorbed through a thickness thereof, and transporting such slide into a processing tool having first and second imaging stations. A first surface of the sample slide is imaged by providing the sample slide in the first imaging station whereby a first lighting assembly illuminates a second surface of the sample slide while a first camera captures a first image of the absorbed specimen on the first surface of the sample slide. A second surface of the sample slide is imaged by providing the sample slide in the second imaging station whereby a second lighting assembly illuminates the first surface of the sample slide while a second camera captures a second image of the absorbed specimen on the second surface of the sample slide. Data of the first and second captured images is transmitted to a computing device having a set of instructions, and using this set of instructions, data of the first and second captured images is analyzed to determine and identify a location of the absorbed specimen for removal. The identified location of the absorbed specimen on the slide is then removed for subsequent processing.

In one or more embodiments, the first and second lighting assemblies may be independently operable and adjustable for capturing various parameters of the absorbed specimen. The first and second images may be captured sequentially, or they may be captured simultaneously. In certain embodiments the methods may further include determining hematocrit level data of a dried blood spot including, but not limited to, color data and viscosity data.

The methods may also further include analyzing and comparing the first image of the absorbed specimen on the first surface against the second image of the absorbed specimen on the second surface to determine a flow pattern of the absorbed specimen through the sample slide. In doing so, the saturation volume area may be calculated using at least the differential between the first image and the second image in combination with a thickness measurement of the sample slide. In one or more embodiments, the invention includes a sample slide containing a specimen including permanent laser markings that at least uniquely identify the specimen on the sample slide.

The invention is still further directed to computer system that includes a central processing unit (CPU), a computer readable memory, and a computer readable storage media. The system also includes first program instructions to retrieve first imaging data of a first image of a specimen on a first surface of a sample slide, second program instructions to retrieve second imaging data of a second image of the specimen on a second surface of the sample slide, and third program instructions to analyze the first imaging data and second imaging data, alone and against each other, to determine and identify a location of the specimen on the sample slide for removal. The first, second, third and fourth program instructions are all stored on the computer readable storage media for execution by the CPU via the computer readable memory.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 1A is a perspective view of a filtration media slide suitable for use in the present invention.

FIG. 1B is a top view of the front side of the slide of FIG. 1A having a fluid sample deposited on the filtration media.

FIG. 1C is a cross sectional view of the slide of FIG. 1A showing the flow pattern of the deposited fluid sample traversing through a thickness of the filtration media.

FIG. 1D is a bottom view of the backside of the slide of FIG. 1A having the deposited fluid sample.

FIG. 14 are charted test data results of imaged front side DBS slides showing the spread patterns of low hematocrit blood samples as compared to high hematocrit blood samples.

DESCRIPTION OF THE PREFERRED EMBODIMENT(S)

Figure 1E:
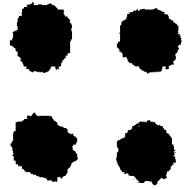
FIG. 1E shows a number of front side (top) and backside (bottom) views of sample spot images taken in accordance with one or more embodiments of the invention.
Figure 1E:
Figure 1E:
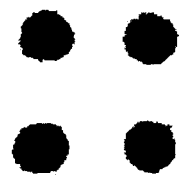
Figure 1E:
Figure 1E:
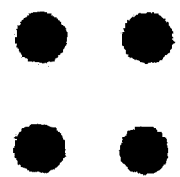
Figure 1E:

In describing the preferred embodiment of the present invention, reference will be made herein to FIGS. 1A-16 of the drawings in which like numerals refer to like features of the invention.

Terms such as "above", "below", "upper", "lower", "inner", "outer", "inwardly", "outwardly", "vertical", "horizontal", and the like, when used herein, refer to the positions of the respective elements shown on the accompanying drawing figures and the present invention is not necessarily limited to such positions. In the embodiments of the present invention described herein, it will be recognized that individual elements and/or features thereof are not necessarily limited to a particular embodiment but, where applicable, are interchangeable and can be used in any selected embodiment even though such may not be specifically shown.

The desire and need to use dried blood spots (DBS) has been steadily rising in both preclinical and clinical applications in lieu of plasma. DBS is a dried sample of blood, typically small in size and often containing one or more analyte(s), that is stored on a slide. In typical sample analysis methods, a small portion of the DBS sample is punched from the slide. However, questions have been raised as to how the obtained sample portion relates to the total DBS portion, and if a variety of DBS locations may be selected from on a DBS slide, how to determine which DBS sample to choose and/or which portion of such a chosen DBS to punch.

In clinical trials of a new drug analyte, various patients are enrolled to test the effects of the analyte. The physical effects are monitored, but to have meaning, they must be related to the amount of analyte in the patient's bloodstream. The analyte is typically carried by red blood cells, which is measured by the patient's hematocrit. This is a measure of the percentage of the red blood cells in the bloodstream.

Currently, primarily LC-MS/MS, the analyte in dried blood spot (DBS) can be quantitated. However, when comparing the effects of the analyte on two different patients, an estimate of hematocrit is required. Patient A having a high hematocrit will show more analyte than Patient B having a low hematocrit. Thus, to compare results an estimate of the sample hematocrit is required to correctly determine the effect of the measured drug on each patient.

With dried blood spots the only resource available is the image of the blood spot, plus the available physical data including, but not limited to, volume applied, filtration media, etc. The present invention provides access to this resource(s) via independent camera systems that analyze the image from the front side where the sample was applied, and from the backside where the applied sample soaked through the filtration media.

Hematocrit levels have two defining physical characteristics, namely, color and viscosity. Fewer red cells and a lower hematocrit provide a brighter red image. It also has less viscosity. Conversely, a higher number of red cells has a higher viscosity and is noticeably a darker red. This difference in color, which is controlled through lighting in accordance with the invention, allows one to define and measure variations in color.

The other hematocrit variable is viscosity. This can be measured with various filtration media through fluid mechanics. The less viscous liquid will flow differently within the confines of filtration media. The high hematocrit, more viscous liquid, will flow in a different manner in the same media.

The problem with using color to measure hematocrit is that other factors can alter the color in a specific sample. For example, the amount of oxygen in the bloodstream. Thus, while color relates directly to hematocrit, there is not a common color scale from one patient to the next. Viscosity, however, is more directly related to the percentage of red cells, which is measured by hematocrit. By utilizing different grades of filtration media, the gathered and recorded data establishes a more defined and reliable marker for hematocrit. With sufficient data over many samples, viscosity data may be used to relate to a common color scale for various patient hematocrits. The combined data from the color results and the viscosity results provides a higher level of confidence in the ultimate end results.

In one or more embodiments of the invention, each DBS is analyzed to determine the hematocrit levels for each DBS or the hematocrit levels residing across and within a single DBS. A high hematocrit in the DBS sample corresponds to such DBS sample having a large amount of red blood cells, as compared to a DBS sample having a low hematocrit. Red blood cells absorb more analyte as compared to white blood cells. As such, a DBS sample or portion thereof having a high hematocrit will have more red blood cells, and in turn, more analyte.

In accordance with embodiments of the invention a DBS sampling system is provided having dual camera systems for imaging and analyzing a DBS prior to taking a sample therefrom. In one or more embodiments, a first camera system of the present systems is positioned over a first side of a DBS slide (i.e., a front side of the slide) while the second camera system is positioned over an opposite, second side of the DBS slide (i.e., a backside of the slide). As discussed in more detail below, each separate camera system at the front and back of the slide has at least its own independent lighting control.

For bioanalytical evaluation of dried blood spots, embodiments of the invention capture one or more images of a DBS on a slide, both at the front side and backside of the slide. That is, a number of different images of each DBS may be taken at the front and back of the slide. For each of these images, processing parameters of each respective camera may be adjusted to capture images using a variety of imaging effects to obtain additional data of the DBS. These imaging effects may include taking images at various adjusted camera controls including, for example, gain, color, hue, brilliance, and the like. In doing so, both cameras will detect and capture additional imaging data detail (e.g., color/hue differentials within the sample) that otherwise would not be available to the naked eye. Camera controls may also be adjusted by changing imaging pixilation to capture various images at different pixels. This captured DBS image data may be used to calculate the area of the actual DBS deposited onto the slide.

The captured image(s), along with various image data, are stored in a database of the present DBS sampling systems for analysis thereof. This dual-captured DBS imaging data is evaluated to determine a number of parameters including, but not limited to, whether the sample soak into the slide, whether the sample spread-out on the slide, color/hue differentials within the sample, and the like. It should be appreciated and understood that various other parameters of the captured DBS images may be analyzed in accordance with the invention depending upon the desired end result.

The captured image(s) and the analyzed parameters of such captured images are used to select the specific area of the DBS on the slide to be sampled prior to the analysis thereof. Depending upon the end-analysis that is to be performed on the DBS, one, more and/or various combinations of the analyzed DBS imaging parameter data may be used to determine the exact DBS location on the slide to punch for analysis.

For instance, red cell levels of the blood sample are often crucial since high red cell levels reflect high levels of analyte absorbing red blood cells. In instances when it is desired to test a blood sample for an analyte of interest, a DBS sample location having high red cell levels may be desired as such a punched location will provide easier analyte testing and more reliable test results thereof. The present invention analyzes the captured images, from both the front and back of the slide, by analyzing detected image parameters thereof. In doing so, the invention determines those locations of the DBS sample that are darker in hue (color) and less brilliant, both of which reflect regions of the DBS sample having high red cell levels. These regions of the DBS sample having high red cell levels may be selected and punched for analyte analysis.

The invention also utilizes other DBS parameters for determining where to punch the DBS slide. In addition to determining those DBS regions having high red cell levels, the invention also analyzes absorption patterns of the blood sample on the slide prior to punching. Blood samples having higher red cell levels are more viscous than blood samples having low red cell levels. The dual images captured at the front and back of the slide include pixel data, which is used to determine the flow pattern of the sample through the filtration media of the slide prior to punching. For instance, the pixel data at the front and back of the slide may be used to determine whether the deposited blood sample spread out and/or soaked through the filtration media, both of which are parameters used in accordance with the invention to determine where to punch and obtain a suitable sample from the DBS for subsequent analysis thereof.

Other factors are taken into consideration in the determination of flow pattern of the sample through the slide filtration media. Predetermined or known properties and characteristics of the filtration media of the slide are input into a computing device of the invention and used in the determination of flow pattern of the sample through the media for selecting a location to punch. In one or more embodiments, the properties and characteristics of the filter media may include porosity and thickness of the filtration media, both of which affect flow characteristics of the various samples through the filtration media, particularly in view of the different viscosities of such samples.

Another factor implemented in determining a location to punch is the total of volume of sample deposited onto the filtration media. With the volume of deposited sample being a known variable prior to depositing, the present system may calculate the percentage of the total sample that was actually analyzed. Again, the dual camera systems of the invention capture and measure the entire sample area at both of the front and back of the filtration media. Often, the front and back pixel areas of the samples are different with the front (or deposition side) of the media having the sample dispersed over a larger surface area as compared to the back of the media. Once deposited, the sample may tend to flow through the media in a conical shape. Knowing the thickness of the filtration media and the sizes of the surface areas of sample at the front and back of the media, the invention calculates an approximate saturation volume area of filtration media saturated with sample. In doing so, a frustum of a cone volume area is estimated within the filtration media, which may also be used in determining the exact location to be punched for sample removal.

It should be appreciated and understood that a number of other parameters and variables may be used to determine the exact location on a filtration media where a sample is to be removed (e.g., punched). It should also be appreciated and understood that the invention may further include a calibration period during which a closed control logic feedback loop determines a best location for removing samples for a batch of filtration media slides to achieve a desired end result test analysis (e.g., a desired output analyte recovery). This closed control logic feedback loop may use input parameters that will provide optimal output results (e.g., optimal recovery of an analyte).

This calibration period may be achieved through end-user (i.e., operator) input in combination with system logic. For instance, the dual cameras may display to the end-user images of one or more deposited samples at both a front side and backside of the slides. The end-user may select a desired area for spot selection. The camera software defines and records the image details of the selected spot, and then such selected spot is punched and analyzed. The end results are rated by the operator and recorded within software of the invention. Over a period of time involving the processing of a number of samples, a correlation between input parameters and output results is obtained for determining best locations to punch samples. Once it has been determined that optimal end results have been achieved, correlation between such optimized results and the locations on the slide at which the samples for such optimized results were taken from the slide are identified and stored for subsequent sample analyses.

Without departing from the novel concepts of the invention, while the invention is described herein with respect to blood samples (i.e., dried blood spots (DBS)), the invention may be implemented with any type of sample suitable for use with filtration media slides. A variety of dried matrix spots (DMS) may reside on a filtration media slide, and may be used in the present invention. These DMS may include one or more purely biological samples, one or more purely chemical samples, or the specimens may be a combination of one or more biological and chemical samples. For instance, a purely biological sample may include, but is not limited to, blood, saliva, bodily secretions (e.g., tears, synovial fluid, urine, semen, etc.), organic matter, and the like. A purely chemical sample may include, but is not limited to, a drug, an analyte, an organic or inorganic chemical compound, and the like. A sample that includes both biological and chemical components, may include, but is not limited to, a blood sample being tested for presence of a drug, bodily secretions being tested for presence of an organic or inorganic chemical compound, such as, a contaminant (e.g., a poison), and the like.

Referring now to the drawings, dried blood spot (DBS) samples are provided on filtration media slides. FIG. 1A shows an example of such a filtration media dried specimen storage slide which is disclosed in U.S. patent application Ser. No. 12/868,229 to Thomas W. Astle filed Aug. 25, 2010, which is herein incorporated by reference in its entirety.

The filtration media slide (1) may include outer rigid frames (2) that encase a sheet of filtration media (3), which is trapped within the ultrasonically welded assembly. For instance, three die cut forms (2) of high impact polystyrene 0.030 inch sheet material may be ultrasonically welded to form the slide (1). Since the slide may contain various filtration media for specific applications, the specific designation of the filtration media (5) may be printed on the slide.

Also the name of the slide manufacturer (4) may be printed on the slide, along with an 12-digit 128 bar code (6) for sample identification. These bar codes (6) may be both machine and human readable. The combination of manufacturer's name and the 128 bar code, combined with the manufacturer's agreement to never print the same identification number twice on this product, assures that there is one positive sample identification from source to discard. This is an essential requirement in a Good Laboratory Practice (GLP) regulated environment. As shown in FIG. 1A, the filtration media (3) may also be printed with a number of regions A, B, C, D that identify locations where a sample is to be deposited, or has been deposited, thereon such media.

To avoid the use of soluble ink, all printing on the polystyrene surface may be accomplished with laser markings to provide permanent identification markings both on the rigid card material itself and on the filtration paper. Laser printing also avoids contact pressure, which may alter the filtration characteristics of the filtration media. A laser may be used to mark the suitable sample targets. The laser is a non-contact printing method that leaves a light scorched marking for identification on the filtration media and/or etching a permanent barcode identifier in the polystyrene frame of the slide. In addition, the laser avoids the use of soluble inks, which may dissolve, dissipate or smear upon depositing the specimen (i.e., organic and/or inorganic specimen) onto the media. By controlling the power applied with the laser, it may be used to simply mark, or it may be used to cut a pattern by burning through.

Additionally, by increasing the power to the laser, the laser may burn through the filtration media in a precisely controlled manner to provide cut out sections in the filtration media which both mark locations where sample specimens are to be deposited and provide for easier and more efficient removal of such marked locations. After the laser cuts through the media, filtration media portions remain as holding tabs at the 12:00, 4:00, and 8:00 o'clock positions.

FIGS. 1B-1E show various views of a sample loaded onto a filtration media slide (1). As is shown, a front side (i.e., top) of the slide is shown in FIG. 1B, which is the side that the sample (100) is deposited onto the media (3). As the sample (100) is absorbed into the filtration media, properties of such sample may cause the sample to spread out over the surface area of the top of the media as it is absorbed therein. FIG. 1D shows the backside (i.e., bottom) of the deposited sample (100) of FIG. 1B, while FIG. 1C shows a cross sectional view of the sample (100) traversing through a thickness of the media (3). As is shown, the sample absorbs into and through the thickness of the media in a conical shaped pattern. In doing so, the absorbed sample (100) at the back of the media may have a smaller surface area as compared to the sample surface area on the front side of such media.

Again, using these front side and backside sample surface areas obtained in accordance with the invention, the invention estimates the frustum of a cone volume area within the filtration media to identify a location of the absorbed sample that will provide a sufficient sample size with the desired characteristics for the removal thereof. FIG. 1E shows front side (top) and backside (bottom) views of images taken in accordance with the dual camera system of the invention. As is shown, the sample absorbs differently into and through the filtration media depending upon the characteristics and properties of the media itself, as well as depending upon the characteristics and properties of the sample being absorbed therein filtration media.

Figure 2:
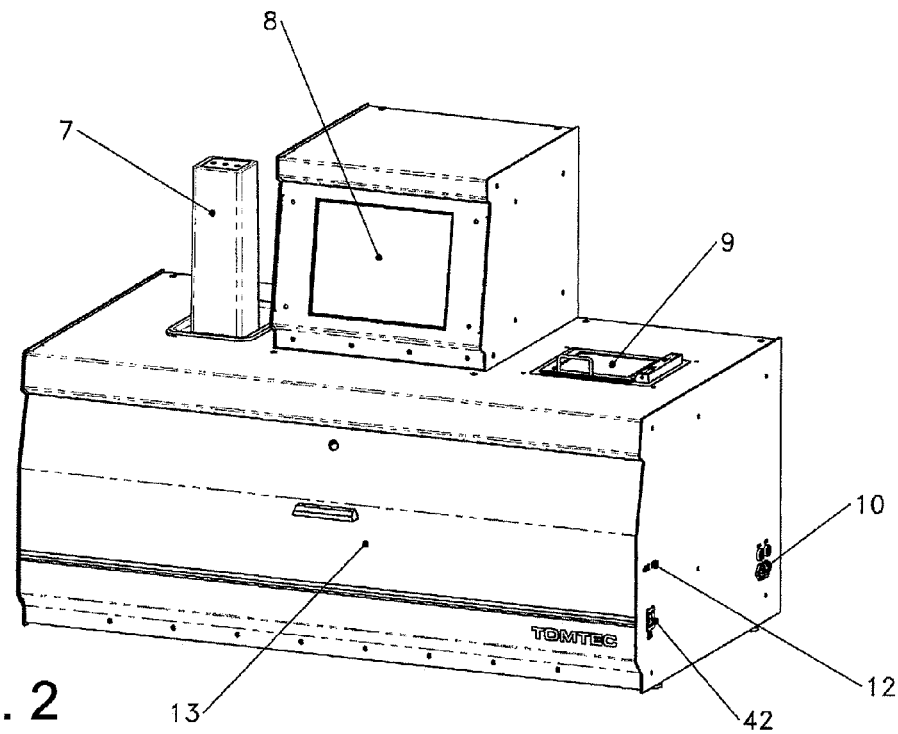
FIG. 2 is a perspective view of an automated filtration media handling system in accordance with one or more embodiments of the invention.

FIG. 2 is a perspective view of one or more automated handling processing systems in accordance with the invention. These systems include hardware, software and logic running on such systems for handling and processing filtration media slides (1) in accordance with the invention. The incoming sample slides may be contained and transported within a cassette (7) that holds numerous incoming filtration media slides (1). For instance, the cassette (7) may hold up to about 96 slides. A full color electronic display (8) may be used by the system software control to display results to the end-user/operator.

The systems also include a receiving rack of 96 pipettor tips, or a standard 96 well microplate, which may be operator loaded and retrieved through an access door (9). AC power may be provided by an external fused connection (10). A power on-off switch (42) may be provided as multiple USB ports (12) for connection to and interface with the on board control system. A front access door panel (13) may be provided for maintenance purposes.

Figure 3:
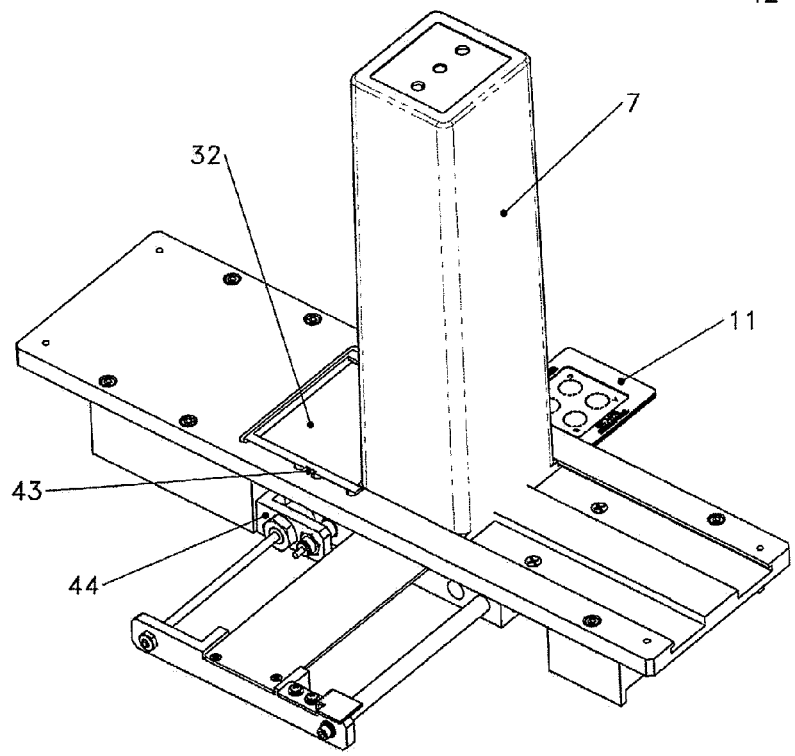
FIG. 3 is a perspective view of a cassette in feed section of one or more embodiments of the invention.

Referring to FIG. 3, a perspective view of the cassette infeed/outfeed station is shown with the cassette (7) of slides placed on the station. The cassette may be moved forward. As the cassette is moved to the infeed/outfeed positions, the cassette lid (32) is retained by mating tabs and slots (43). A controlled pneumatically driven slide component (44) moves an incoming sample slide (11) containing a sample to be processed to a first imaging position (46), as is shown in FIG. 4.

Figure 4:
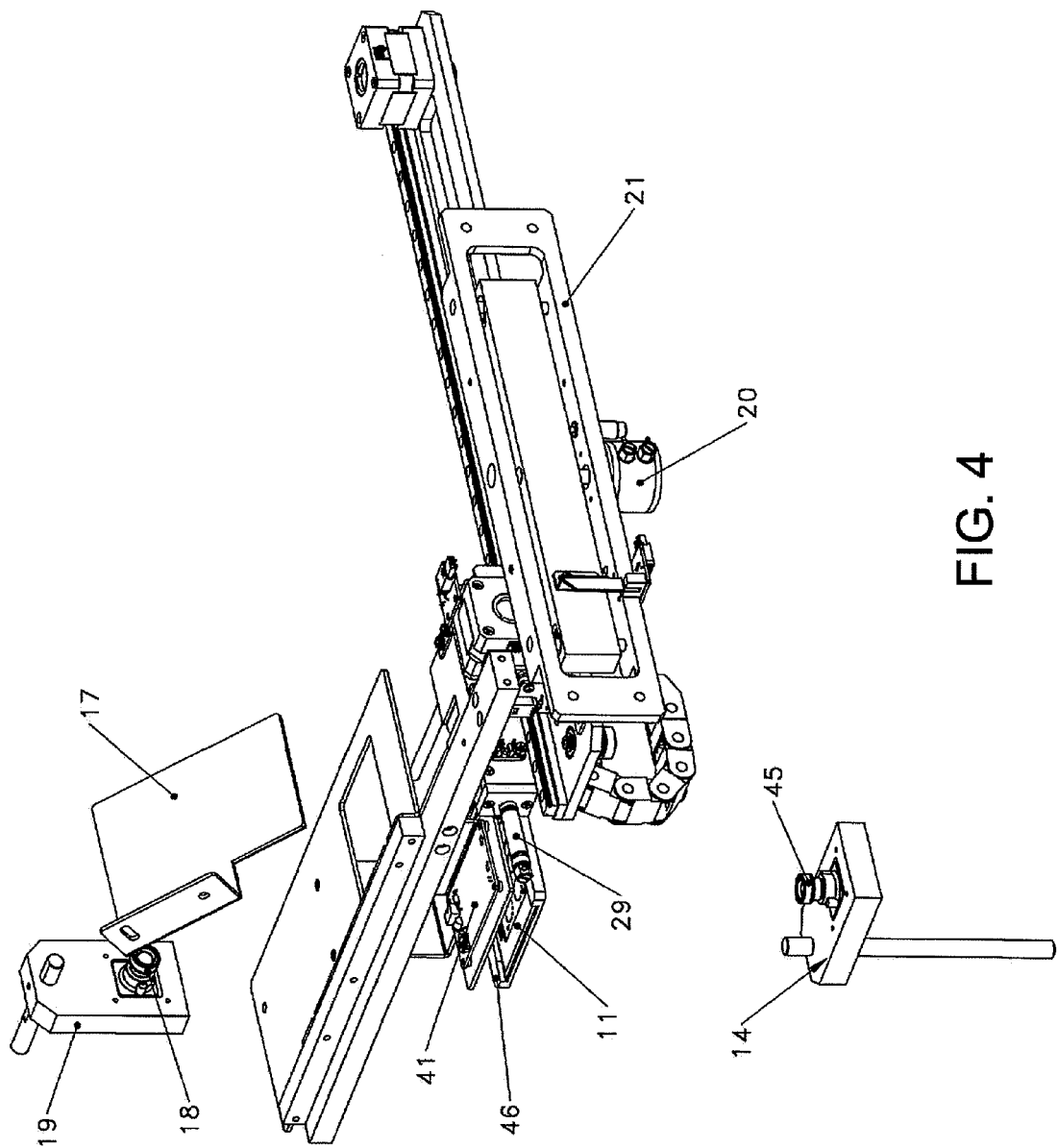
FIG. 4 is a perspective view of a lower camera (backside camera) of the dual camera system of one or more embodiments of the invention.

FIG. 4 is a perspective view of the backside (i.e., bottom side) camera station of the present systems having dual camera stations, one at the front side and the other at the backside of the slides to be processed. As is shown, a software controlled LED lighting assembly (41) provides controlled illumination to the front side of the incoming sample slide (11). At the opposite backside of the incoming sample slide (11) resides the bottom side camera (45). The bottom side camera (45) is mounted at a focal length to image the backside (i.e., bottom side) of the incoming sample slide (11). Another software controlled LED lighting assembly (14) provides controlled illumination to the backside of the incoming slide (11) for capturing such image.

Figure 5:
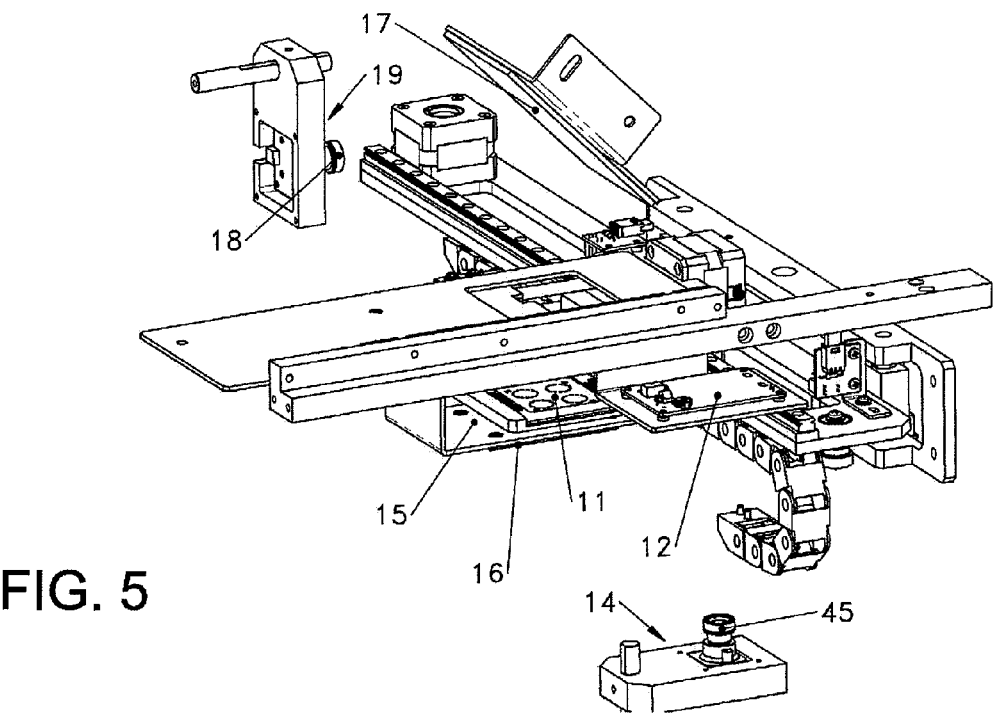
FIG. 5 is a perspective view of an upper camera (front side camera) of the dual camera system of one or more embodiments of the invention.

After the image of the backside of the sample slide (11) has been obtained, the sample slide (11) is moved to a second imaging position to image the opposite side of the slide. Referring to FIG. 5, the sample slide (11) is moved to second imaging position (15) for imaging the front side of the incoming sample slide. This second imaging position (15), or station, also includes a software controlled LED illumination system (16) to illuminate the backside of the incoming slide for capturing the slide's front side image. As shown, the slide (11) is positioned over the backside illuminator (16) for capturing the front side image.

In accordance with the invention, for both front side and backside imaging, during the process of taking such images the lighting assembly on the opposite side of the camera taking the photograph of its respective side is turned on during such imaging to capture color variations within the spots. That is, when photographing the backside of the incoming sample slide (11) only the front side lighting assembly (41) is illuminated while the backside camera captures an image of the spot on the filtration media backside. Conversely, when photographing the front side of the incoming sample slide (11) only the backside lighting assembly (16) is illuminated while the front side camera captures an image of the spot on the filtration media front side. An additional imaging process may also need to be taken of the front side of the slide using both the front side (41) and backside (16) lighting assemblies to capture any identification information residing on the slide front side (e.g, bar codes, sample identification code, etc.)

While the first and second imaging positions or stations are described as respectively obtaining backside and front side images of the slide, it should be appreciated that the first imaging position may capture the front side while the second imaging position captures the backside of the slide (11). Due to the instrument height limitations and the front camera focal length, a mirror (17) may be used to image the slide front side. As with the backside camera, a similar LED illumination system (19) may provide front side illumination for the front side camera (18).

Figure 6:
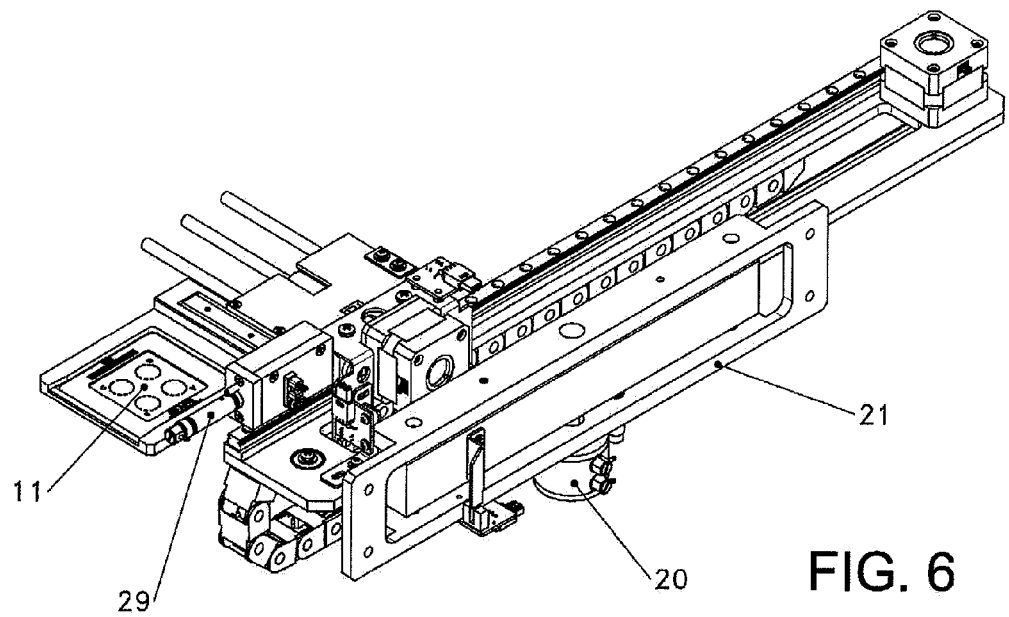
FIG. 6 is a perspective view of a transport component for transporting incoming sample slides into the present systems.

FIG. 6 shows the transport component of the present systems for transporting incoming sample slides (11) to various positions and stations in x-y-z-directions within such systems. The transport component may include two stepper motors that provide controlled positioning motion in both the x and y directions. The transport component is able to move in the z-direction via a small pneumatic cylinder (20) to allow for moving the slide (11) into a punching position.

When the slide (11) is presented to the punching station, there must be clearance to insert the slide between the punch and mating die. However, to punch the desired x-y coordinates of the filtration media, the media must be in physical contact with the surface of the die to avoid tearing the filtration media. This required z-motion is provided by the air cylinder (20). It moves the x-y bridge assembly vertically within the supporting framework (21).

Figure 7:
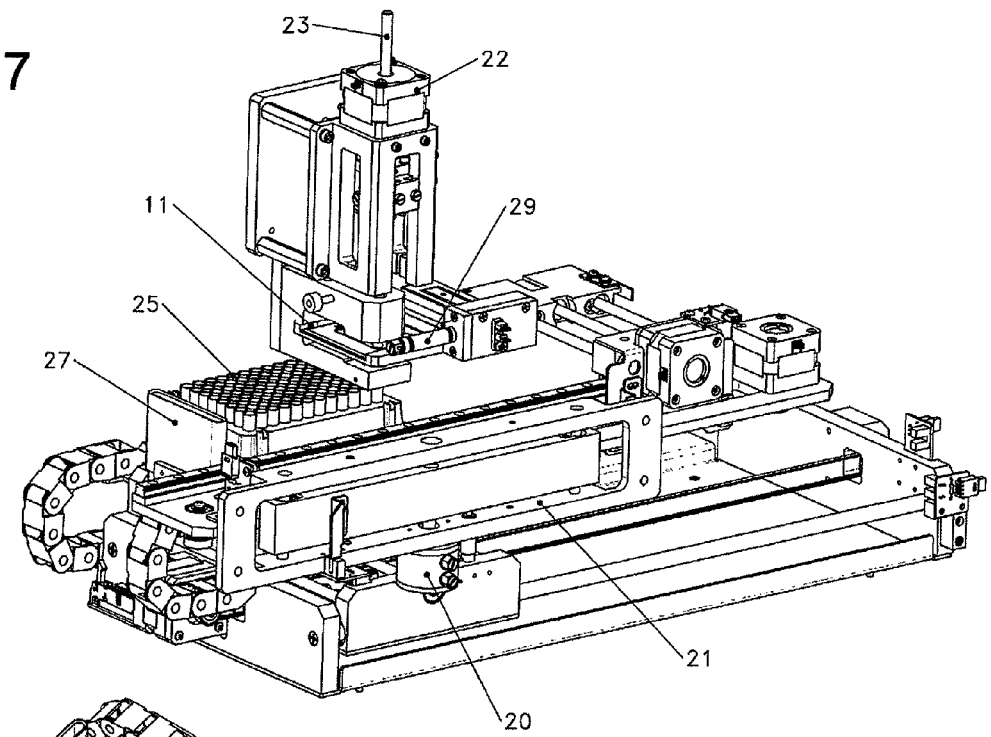
FIG. 7 is a perspective view of a punch assembly of the system of one or more embodiments of the invention.

FIG. 7 shows a perspective view of the punch assembly of the invention. The punch assembly includes an axial stepper motor drive (22) that moves the punch assembly (23) through the sample slide (11), through the mating die and into the receiving receptacle below. The punch has a central hole through which a low power laser shines.

This central hole may also be connected to a vacuum source and a source of low air pressure (not shown). The stepper motor control positions the punch, and at the point of contact between the punch face and the filtration media a solenoid valve applies vacuum to the central hole of the punch. The vacuum assists in holding the punched chad (piece) to the face of the punch for transport to the receiving location. Concurrently, the vacuum source is applied to small holes surrounding the die (not shown). The purpose is to capture any airborne particulate matter that is discharged by the punching action. This vacuum assisted airflow is discharged to the atmosphere through a HEPA type filter to capture infectious material.

At the bottom of the punch stroke the vacuum in the central hole is replaced with a puff of positive air pressure to assist in discharging the punched chad into the receiver. The punch withdraws sufficiently to allow the receiving receptacle to move clear of the punch. This allows the low power laser shining through the bore of the punch to illuminate a sensor that verifies to the system logic that the punch and sample transport and receipt have been completed.

Figure 8:
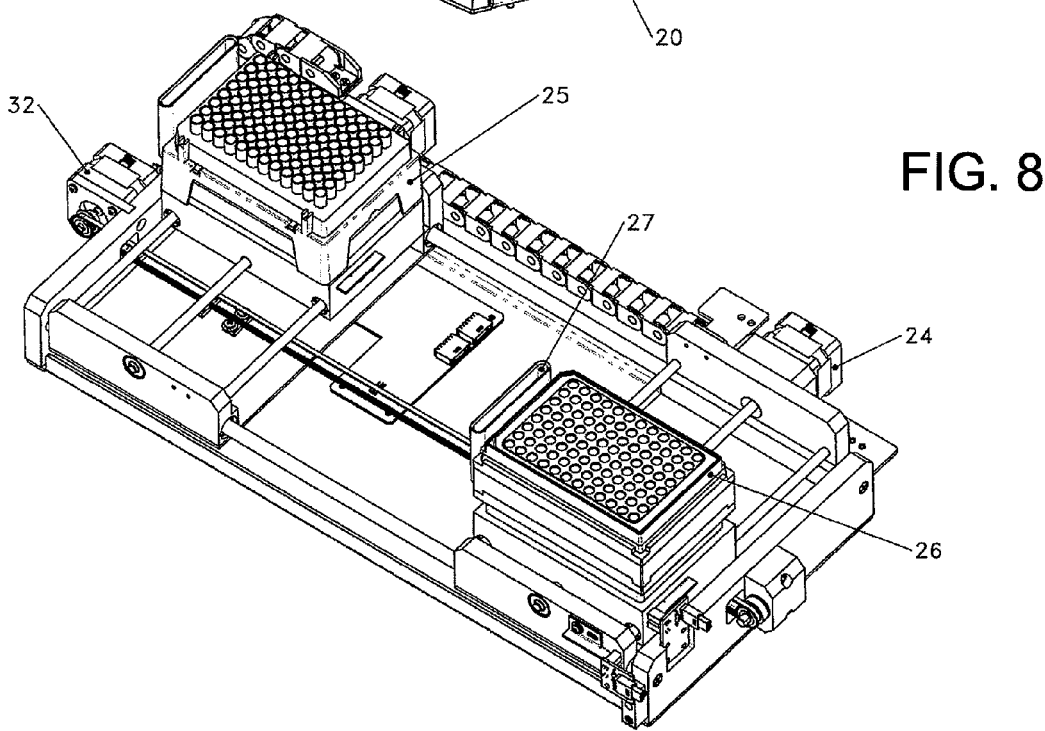
FIG. 8 is a perspective view of an x-y bridge system of one or more embodiments of the invention.

FIG. 8 shows the x-y bridge system for the receiver of the invention, which includes two stepper motor drives for positioning control. One motor (32) provides controlled motion in the x direction, while the other motor (24) provides controlled motion in the y direction. The carrier may accommodate a rack of 96 pipette tips (25), or it may accommodate a standard 96 well microplate (26). The receiving well, or tip, is properly positioned by the associated software and electronic controls of the present systems.

When punching samples from filtration media with the same punch and die systems, there is always a concern about sample carry-over between samples. To avoid these problems the present systems and methods include a step of punching a blank area of filtration media to assist in cleaning the system to minimize the possibility of sample carryover. A trash receptacle (27) of the present systems is moved into position by the receiving bridge system to capture the punched chad.

Figure 9:
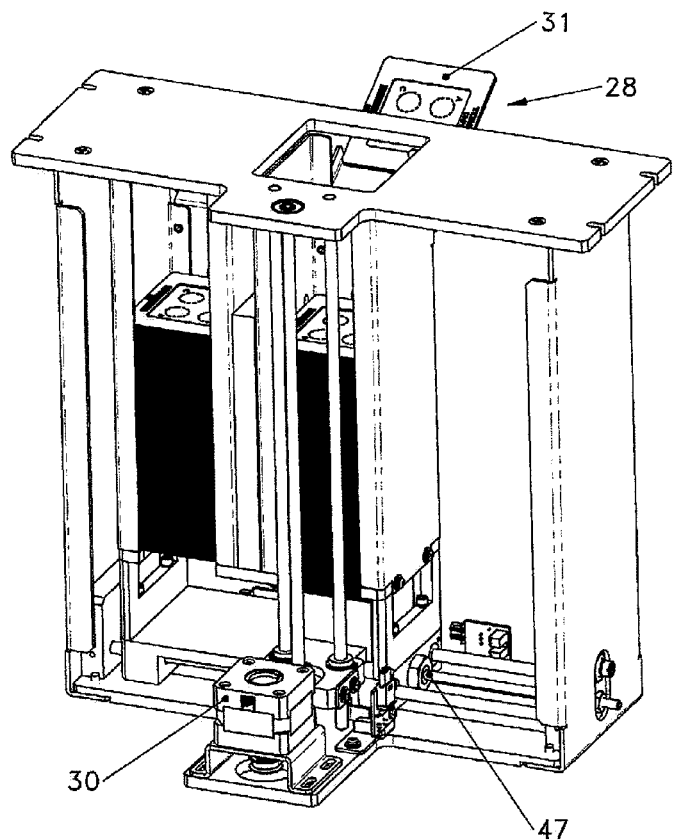
FIG. 9 is a perspective view of an output stack assembly of one or more embodiments of the invention.
Figure 10:
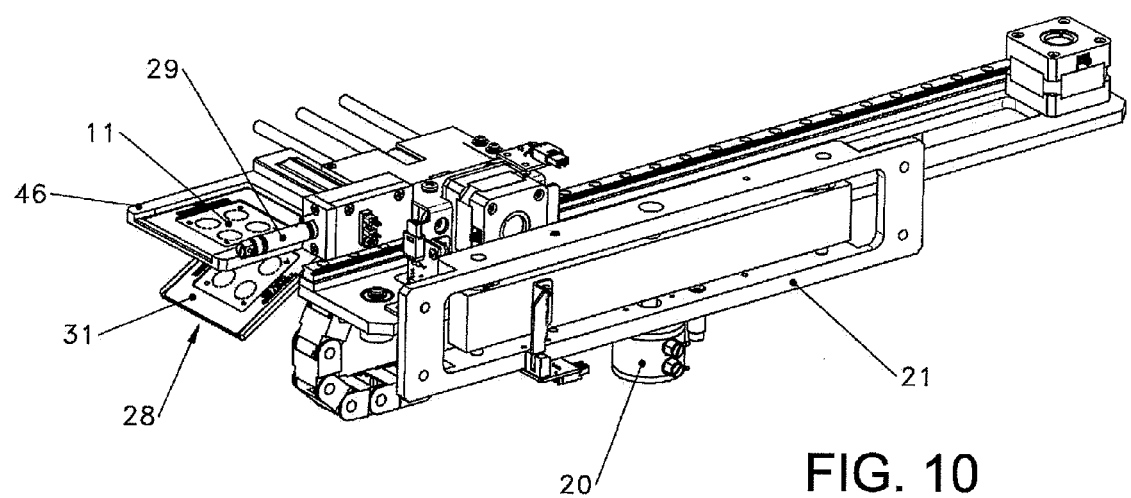
FIG. 10 is a perspective view of a slide handling x-y-z assembly of one or more embodiments of the invention.

After the punching cycle is complete, the slide is returned to the front side camera station (46). A second front side image may be captured to document the location of the sample that was punched. The slide (11) may then be moved to the offload position, as shown in FIG. 10. In offloading the processes sample (11), an air cylinder (29) rotates the slide carrier from position (46) to position (28) to allow the slide, now shown as (31), to move down into the receiving output stack. FIG. 9 shows the output stack assembly. Preferably, slides are then filed and stored within the cassette in their original filing order. The output stack assembly may include two stacks for controlling the height (i.e., amount) of slides within the present systems.

Figure 11:
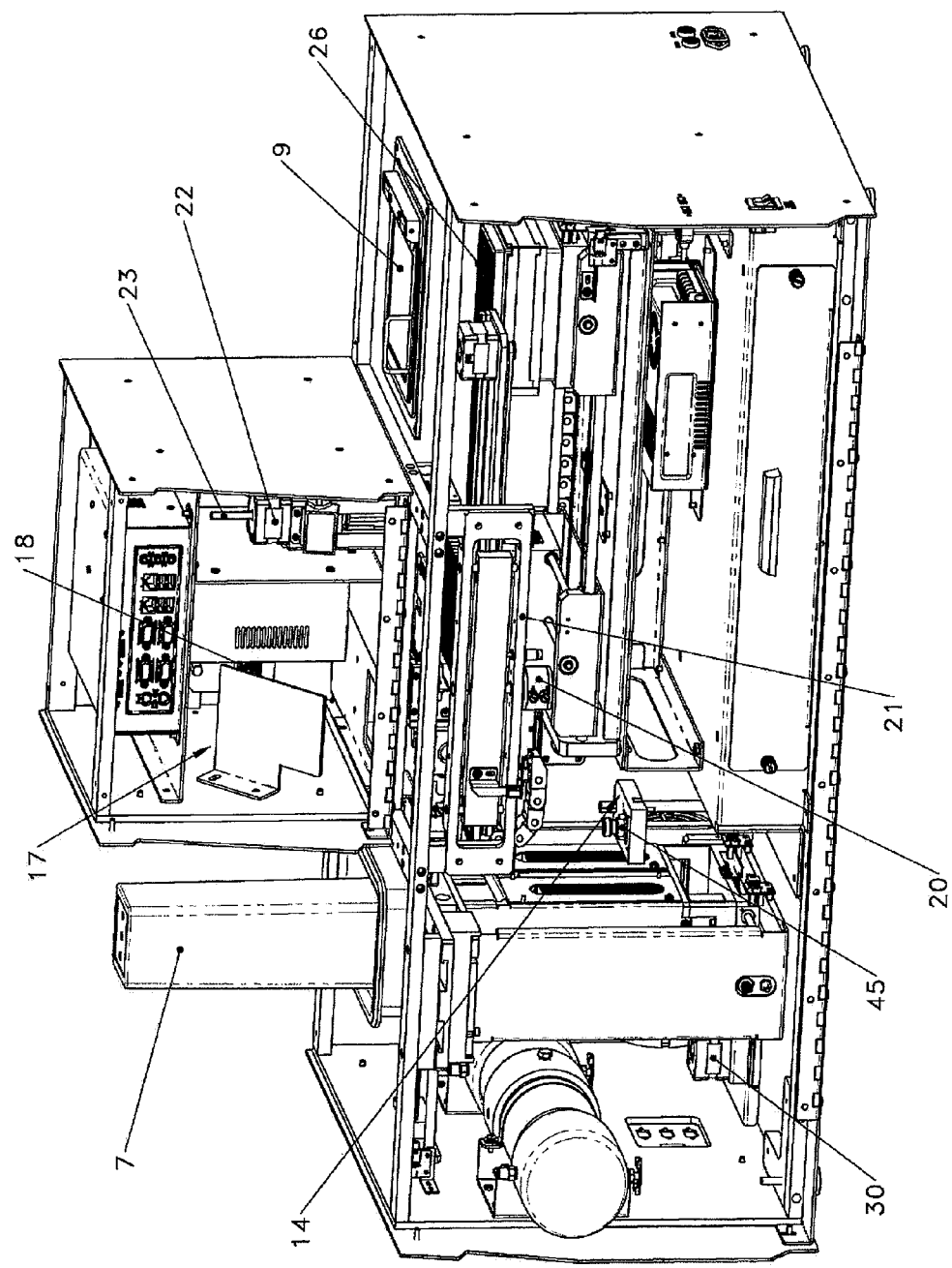
FIG. 11 is a perspective view of an assembled system of one or more embodiments of the invention having front enclosure panels removed to show the relationship of various described sub-assembles or parts of such system.

As the slide carrier (28) drops down to its offload position, the slide (31) it contains drops into the waiting receiver stack. A software controlled stepper motor (30) keeps the receiving stack at the correct height to allow the returning slide (31) to glide in on top of the current stack. This action maintains an orderly stack of receiving slides. When one receiving stack is at its capacity, a pneumatic control system (47) shifts the other stack into position to receive slides. When both stacks are at capacity, the slides are returned to the incoming cassette, which is still in position as shown by FIG. 11.

Once the punched portions of sample slides are removed from the present systems, they may then be used for subsequent analysis such as, for example, analyte recovery. Alternatively, the systems of the invention may be combined with another analytical tool for the directed use of such punched sample. For instance, the systems of the invention may be combined with chromatography instrumentation for the direct elution of the samples immediately after being punched and removed from the slide (11).

As an example, the sample may be directly eluted into the mobile phase of a liquid chromatography (LC) instrument, which is commonly part of an LC/MS/MS analyte detection system. For such an application, the x-y recovery bridge system shown in FIG. 8 may not be utilized or installed, nor is the punch system of FIG. 7. Both are replaced by a break in the liquid connection of the mobile phase going to the LC instrument, as is shown in FIG. 12.

Figure 12:
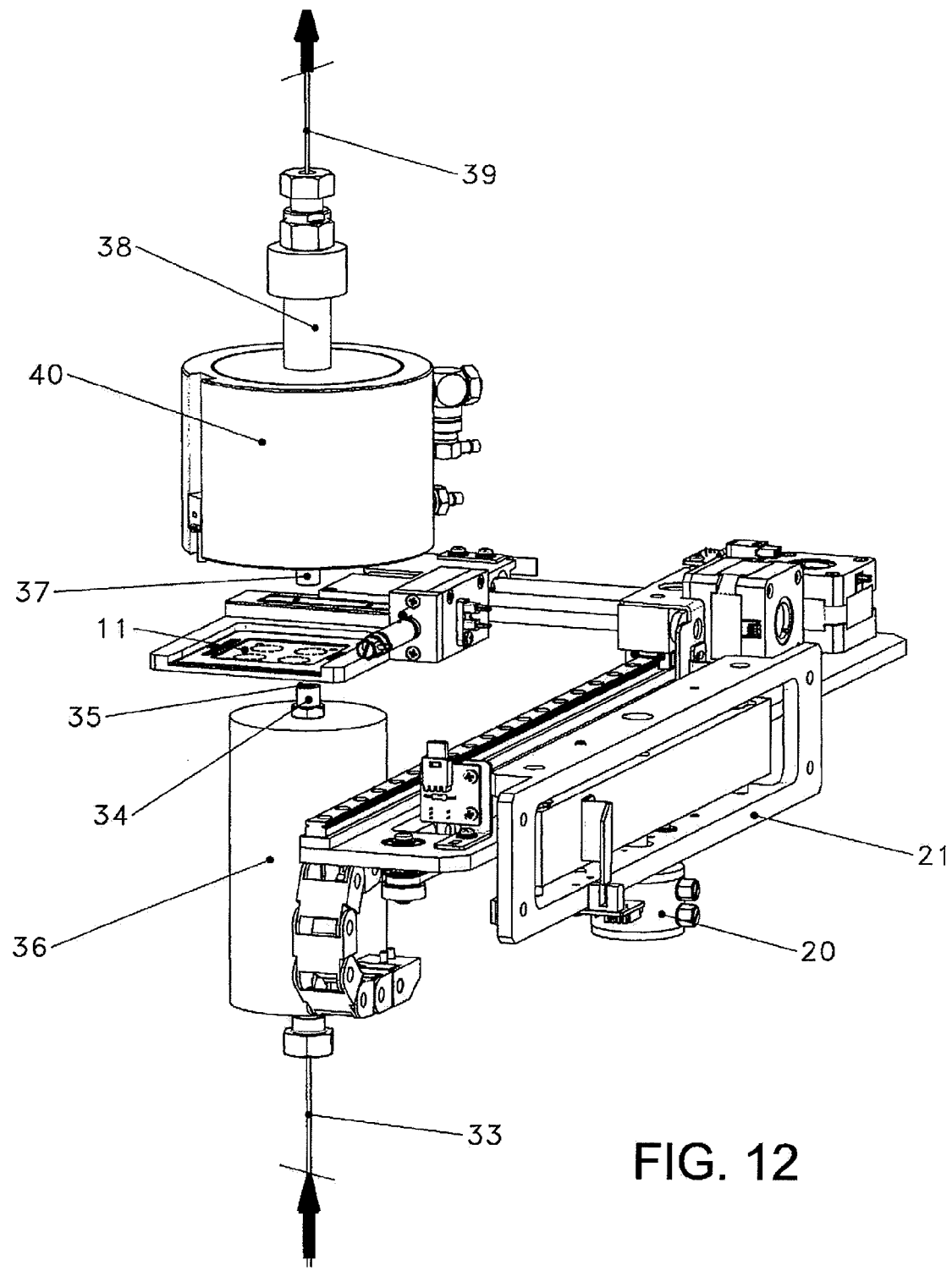
FIG. 12 is a perspective view of a liquid chromatography interface in combination with the various systems of the invention.

Referring to FIG. 12, the incoming side of the mobile phase line (33) terminates at a connection point (34) that is surrounded with an elastomeric O-ring (35). This elastomeric O-ring (35) is mounted on a rigidly mounted support column (36), which is affixed to the instrument framework. The outgoing mobile phase line (39) terminates in a mating elastomeric O-ring (37) that is positioned by the central plunger of a large bore air cylinder (40). The air cylinder may apply sufficient force to cause the mating elastomeric O-rings to create a seal that is sufficient to withstand the internal pressure of the mobile phase.

Still referring to FIG. 12, the selected spot for analysis on the incoming slide is positioned between the mating O-rings by the x-y-z, bridge system (21.) When the selected spot is aligned between the O-rings, the air cylinder (20) lowers the incoming sample slide (11) so that the selected spot is in contact with the lower O-ring (35), which is rigidly supported by the column (36). At this point, the control system applies air pressure to the air cylinder (40) causing the top O-ring (37) to close with sufficient sealing force to withstand the internal pressure of the LC mobile phase system. Concurrently, a confirming signal is passed to the LC mobile phase controller to commence an interface action.

Referring again to the dual camera systems of the invention for taking front side and backside images of the sample slide (11). The dual cameras of the present system(s) capture their respective positioned images of the sample slides (11). Data from the captured images is sent to software and logic components of the invention. The software and logic utilize the various image data parameters, along with other parameters and data, to determine an ideal or desired punch location (i.e., a best punch location) of the imaged sample from which to obtain (punch) a portion thereof for subsequent downstream processing and/or analysis. The other parameters and data that the software and logic may utilize in determining the desired punch location may be input variables including, but not limited to, properties and characteristics of the absorbed sample (e.g., flow rate, viscosity, color, hue, brilliance, etc.), properties and characteristics of the filtration media (e.g., pore size, thickness, composition, etc.), or even combinations thereof.

While images are captured in pixel data, the software and logic of the invention converts such data for easier use and interpretation thereof. That is images are captured in pixel data, including the area of the captured sample image being captured in pixel area data. Pixel area is a function of the focal length of the camera system used for the image. As such, each of the dual cameras may be calibrated using a square piece of aluminum machined to measure exactly 1.000 inch by 1.000 inch. Using this calibrated measure, along with the pixel area data of each image, the software and logic converts the pixel data into area measured in square inches (i.e., in$^2$). The software and logic may even further convert the inches$^2$ measure into an equivalent "diameter" measure for an easier interpretation thereof. As used and defined herein, the term "diameter" is an area measurement, not a length measurement. For instance, a "diameter" of 0.250 inches is easier to relate to than an area of 0.0490 in$^2$. The following equation may be used for such a conversion into "diameter" of the deposited sample:

$$A = \frac{\pi D^2}{4} \text{ or } D = 2\sqrt{A/\pi}.$$

In certain embodiments of the invention, the systems having the dual cameras and software were employed to determine variables that affect the deposition, absorption and pattern effects of blood spots on filtration media slides. In particular, the systems of the invention were implemented to determine how hematocrit values of blood samples affect the deposition, absorption and pattern effects of deposited blood spots for determining a best punch location from such a DBS. Again, this best punch location will depend upon the ultimate end analysis that is to be performed on the punched specimen or desired result thereof.

Figure 13:
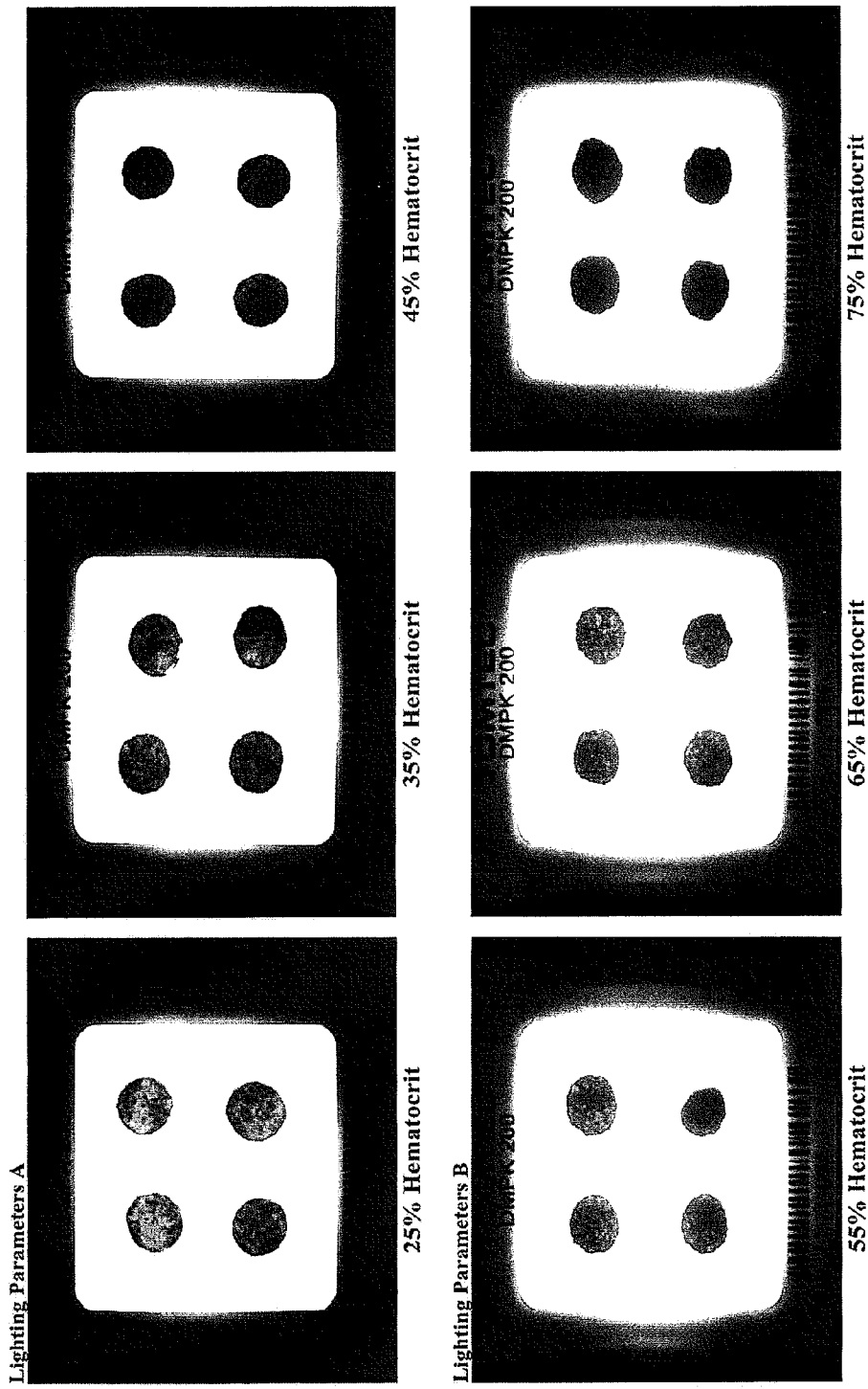
FIG. 13 shows various imaged blood sample spots having different coloring throughout such samples depending upon the amount hematocrit within such samples.

Those DBS samples having higher hematocrit values (i.e., more red blood cells) will be darker in color, and samples having lower hematocrit values will be lighter in color. These darker and lighter image colors can be seen with the naked eye. See, for example, FIG. 13 showing gray areas having lower hematocrit value as compared to black areas having higher hematocrit values. However, much more detailed data relating to such DBS spots can be obtained using the present invention for obtaining the best punch location for each DBS spot.

In one or more embodiments of the invention the dual cameras, software and logic are used to image the front and back sides of the slide, store the image result data, and analyze such image data to determine the front diameter of the DBS sample, the front-to-back differential of the deposited sample, and the color of such sample. All of these parameters are used by the software and logic of the invention to determine the best punch location that includes a desired sampling of the DBS spot that is entirely penetrated with the blood sample. That is, in one or more embodiments, the punched sample may be completely covered with the blood sample throughout its entire thickness, such that, no untreated filtration media material resides within such punched sample.

As discussed above, the front side of the DBS sample is that side of the filtration media that receives the liquid sample. In estimating hematocrit values, the front "diameter" (which again is defined herein as an area measurement, not length) of the DBS sample is obtained by comparing the actual volume of sample deposited onto the media to the area of the spot on the front side. The relationship of hematocrit is consistent with basic fluid mechanics, such that, a low hematocrit blood sample has a lower viscosity than a blood sample having a high hematocrit level.

As shown in the test result data of FIG. 14 the thinner, less viscous blood sample will flow more efficiently over the surface of the absorbent filtration media, as compared to a more viscous, high hematocrit blood sample. If a given volume of liquid sample flows easily over the surface of the filtration media, more of the blood sample will absorb into the media at the front side to generate a larger surface area (i.e., diameter) at such front side, which leaves a lesser volume of sample to soak into and through the absorbent filtration media. A more viscous, high hematocrit blood sample will move across the surface more slowly, leaving a smaller front side "diameter." This slower passage across the filtration media allows more time for the sample to soak into the media, creating the backside spot "diameter."

As such, the present systems may be programmed to detect and identify large front side DBS spot "diameters" as compared to the amount of blood sample deposited onto the media, as corresponding to a blood sample having a low hematocrit value. Conversely, a small front side DBS spot "diameters" as compared to the amount of sample deposited may be identified and correlated with the blood sample having a high hematocrit value.

The invention also captures the backside blood sample image to obtain a back "diameter" of the DBS. For a given liquid volume applied to a specific grade of filtration media there is generally a difference in the size of the front side spot as compared to the size of the backside, which is due to the hematocrit value of the deposited blood sample. Again, a low hematocrit value blood sample has a significantly lower viscosity than a blood sample with a high hematocrit level. Assuming that both the circular areas of the front side image and backside image are on a common central axis, the front side and backside image data are used to calculate an estimated volume contained within the spot area, from the front side of the media to the backside of the media. This may be accomplished using a volume formula of the frustum of a cone.

In the above examples, a specific "spot" was selected for analysis, which was only a portion of the total sample of blood spot area. The camera images provide the front "diameter" and the back "diameter" of the image. The thickness of the filtration media in the slide is known using the equation for the mathematical volume of the frustum of a cone, the volume of the sample spot may be estimated:

$$V = \frac{\pi h}{3}(R_1^2 + R_1 R_2 + R_2^2).$$

The answer is in cubic millimeters, within the conic frustum. The actual sample taken by the punch is also a known cylindrical volume:

$$V = \frac{\pi D^2}{4} \times d$$

Thus, the calculated density of the conical volume may be used to estimate the comparable volume within the punch area, which is the selected volume. Since the blood sample does not flow in a precise conical frustum, this calculation provides a valid estimate of the relationship between the total actual sample volume and the specific percent of that total that was actually analyzed.

In calculating saturation volume area, the differential between the first image and the second image, in combination with a thickness measurement of the sample slide, are used to calculate this measure. This calculation of image volume derived from the camera imaging is then compared to actual volume applied to the filtration media to determine the percent saturation of the applied analyte to the actual punched area taken for analyte recovery by such means as LC-MS/MS. For instance, a blood supply spiked with 4000 ng/mL of an analyte (acetaminophen) was analyzed using the conical frustum method to calculate the mathematical volume of the spot in mm3, which is also μL. This data may vary with hematocrit level, as shown in FIG. 14.

Referring to FIG. 14, as an example, 15 μL was applied to DMPK 200, using 25% hematocrit, the conical volume was 19.36 μL. This shows that the applied volume of 15 μL of liquid analyte only occupied 77% of that area. The punched volume, πD2/4, is then taken for analysis. At least mathematically, that volume only has 77% analyte concentration. Using this mathematical data, with a known starting concentration of 4000 ng/mL, a numerical estimate of the analyte may be obtained that the LC-MS/MS will recover. By collecting sufficient data, using known values, the accuracy of those mathematical calculations with acceptable credibility may be defined. That is, if known starting values of analyte are used, one may predict the amount of recovered analyte with acceptable accuracy.

Another method is available that avoids having to estimate the punched spot volume to the total sample volume. This method analyzes the entire sample spot using a laser to make a scorching mark through the filtration media (i.e., make a mark that defines a delineated area within and through the thickness of the media). For example, a 0.250 inch diameter circle may be isolated leaving holding tabs at 12:00-4:00 and 8:00 o'clock (i.e. 120° apart). The sample volume is applied to the central area and is retained by the holding tabs. The entire volume of sample within the 0.250 inch circle is removed for analysis by breaking the three holding tabs. The entire sample is then analyzed, such that, estimations are not performed.

Using the principle of basic fluid mechanics, you would expect to see a difference between the front side spot and the backside spot when a liquid is added to the absorbent material due to several factors including, for instance, media thickness, volume of liquid applied, viscosity of the liquid, etc. By changing the volume of the blood applied to the front side of the absorbent filtration media, combined with changing the absorbency of the media, parameters with which to differentiate the front spot "diameter" and the backside spot "diameter" are provided. This provides a means of measuring the flow characteristics of a blood supply that is related to the hematocrit of the applied sample.

There are some other parameters that will affect this relationship, and they must be controlled to minimize variations in the final result. The blood must be uniformly dispensed in one specific location. Gravity should be the only force moving the liquid down into the filtration media. The volume of blood applied must be controlled. To the extent that these outside variables are controlled, will have an effect on the accuracy of the results. For instance variables such as manual pipetting of samples onto the media may introduce human error into the end results. This may be avoided by implementing the automated slide processing and handling aspects of the invention.

Another distinguishing marker for hematocrit is color. A blood sample with a low hematocrit has a much brighter red color than a sample with a high hematocrit. This is obvious to the human eye. However, it is even more distinguishable to a sensitive camera system, particularly when the lighting and camera controls of gain, hue, brilliance, etc. can be controlled for the specific observation conditions. The color variations observed and detected by the present camera optical systems across the DBS sample spot may have a direct relationship and correlation to the quality of the end-results. For example, for some analyses the darker areas (higher hematocrit values) may produce the best results, while in other analyses lighter areas (lower hematocrit values) might produce the best results.

By adjusting various camera processing parameters, the camera optical system is able to obtain more imaging detail as compared to the naked eye. From a logical viewpoint, the color of the blood spot may vary with volume. However, that parameter is the easiest to control. FIG. 13 shows color images (shown in gray scale) of six different hematocrit values at two different lighting parameters. At lighting parameters A, the naked eye is able to view color differences at the hematocrit levels of 25% and 35%. However, the 45% hematocrit is difficult to observe color differences. By adjusting the lighting parameters to parameters B the naked eye is now able to observe color differences at 55% hematocrit and 65% hematocrit, however, the 75% hematocrit is difficult to see.

The dual camera systems of the invention provide for increased control of the various imaging parameters including, but not limited to, intensity, hue, brilliance, and combinations thereof. As such the images captured by the cameras include much more detailed data of the blood spot than can be seen or detected by the naked eye. This detailed camera imaging data is stored and used by the software and logic of the invention for determining a best punch location.

System software and logic implement all this stored data (i.e., front "diameter" data of the DBS sample, front-to-back differential data of the deposited sample, and color data of such sample) to determine a best punch location of the given sample spot. Again, this best punch location is dependent upon the ultimate end goal or use to the punched portion of the sample spot (e.g., analyte recovery from the punched sample spot portion). The present systems may be fully automated, and as such, calibration and/or preset parameters and data may need to be input and stored within the system logic in order to make such a determination. This is accomplished by a system closed loop feedback process or training period.

To achieve the fully automated systems of the invention, the instrumentation of the system must be programmed, or given guidelines and parameters, for detecting specific spots or locations (i.e., best punch locations) within the sample area to punch for downstream processing. In doing so, an end-user or operator may view and select a number of front side and backside imaged sample spots for punching and analysis to determine which of such punched locations provide test results that fall within a predefined set of parameters for such analysis.

For instance, an operator may select one or more areas of interest from the front side and backside of the slides. The dual camera systems then image these locations and data in relation to said locations are stored. Test samples may be run on these areas of interest to determine whether they provide desired results, or results that fall within a predefined range of acceptable parameters. The test run(s) results are stored within the logic of the present systems (i.e., within a database) for programming the present systems for future runs in locating and obtaining other sample spots that meet or exceed these stored parameters.

After these parameters have been stored within the system logic, and it is determined that acceptable runs are being performed with such parameters, the closed loop feedback process may be ended. The present systems are then fully automated for subsequent runs that simply look for specific input parameters to select the optimum point (i.e., best punch location(s)) to punch for a specific sample on a filtration media slide. These runs may be performed on single, individual slides, or alternatively, batches of slides.

Examples implementing the systems and methods of the invention were performed to determine how hematocrit values of blood samples and how they affect the deposition, absorption and pattern effects of such deposited blood spots. Participants deposited blood samples on three different grades of filtration media to provide a variety of DBS slides for analysis thereof in accordance with the invention. These grades of filtration media included DMPK 200 (0.016 inches thick), DMPK 300 (0.026 inches thick) and DMPK 400 (0.032 inches thick), all of Tomtec.

One aspect of the testing was to determine how hematocrit of the incoming DBS slides affected the absorption of the deposited samples, and in turn, determining a best location for punching a portion of such deposited samples for further processing. Pooled blood samples having 6 different hematocrit values were evaluated, and in particular, hematocrit values of 25%, 35%, 45%, 55%, 65%, and 75%.

Samples were deposited onto the filtration media using a manual pipettor and Aqua Caps. The manual pipettor has the potential of injecting the liquid stream into the media. This can either be due to the rate of dispense, or the use of the second stop, blow out feature. The Aqua Cap is a capillary tube with a calibrated plug. In essence, it is a positive displacement pipettor that is calibrated to contain, as well as to deliver. It is filled by capillary action and dispensed by inserting a plunger to expel the plug. It is less susceptible to injecting the contained liquid into the filtration media. For the study, the Aqua Cap was used as a second control on the method of sample dispensing.

In the study three volumes 15 µL, 25 µL, and 40 µL, of the different hematocrit value containing samples were deposited (alternately using manual pipettor and Aqua Cap) onto the different grades of filtration media; DMPK 200, DMPK 300, and DMPK 400. The dried blood sample (DBS) slides were then processed using the dual camera system and methods of the invention. That is, a first camera system having its own lighting captured images from a front side of each slide, while a second camera system having its own lighting captured the image from the backside of such slide.

Figure 15:
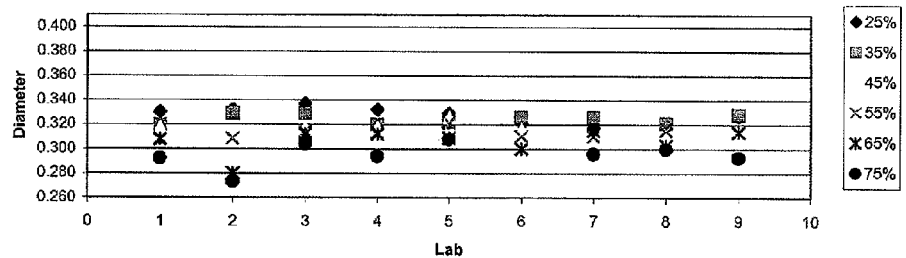
FIGS. 15-16 show test results performed using embodiments of the present methods and systems.
Figure 15:
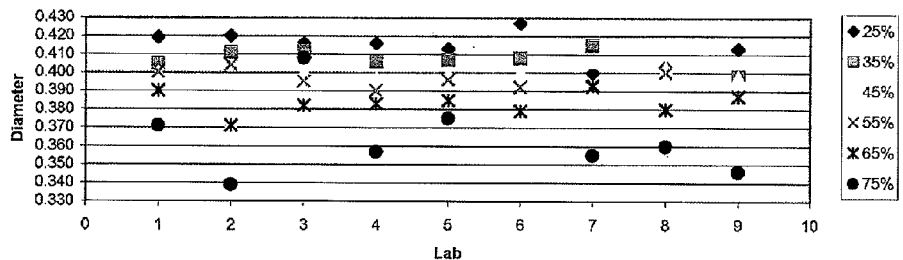
Figure 15:
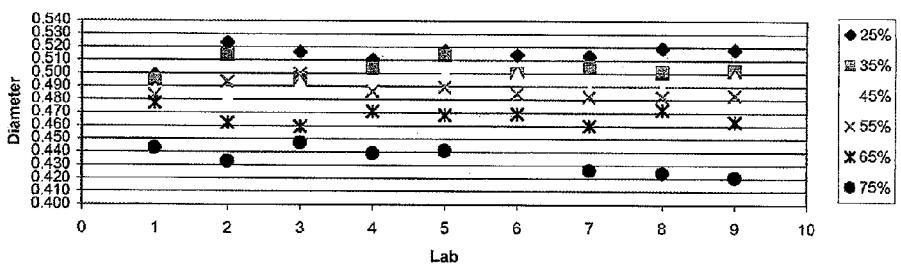

These studies found that the higher the hematocrit levels residing in blood samples, such samples were less spread out over the front side of the filtration media. That is, they had a smaller "diameter" (area) as compared to the less viscous lower hematocrit value blood samples. Likewise, the lower hematocrit value blood samples were spread more easily and were larger in "diameter" (area) across the front side filtration media surface. See, for example, the front "diameter" results of hematocrit value detections for various volumes of differing hematocrit level blood samples deposited by Aqua Cap onto DMPK 200 (0.016 inches thick) filtration media slides as shown in FIG. 15.

Figure 16:
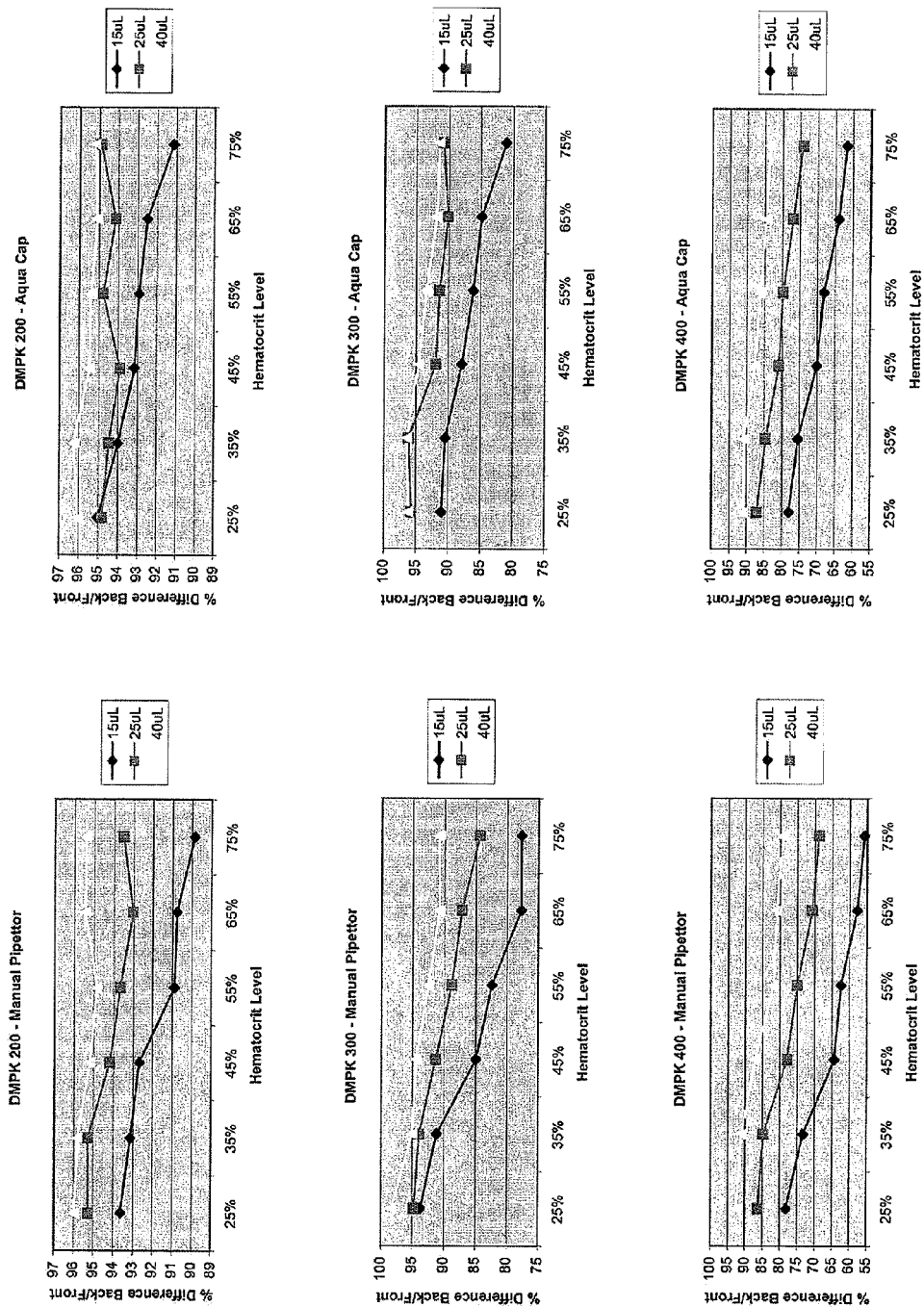

The FIG. 16 results of the "diameter" percent differences from the front side of the media to the backside of the media also show that the greater the volume of sample deposited onto the media, the greater the difference between the front and backside "diameters" of the DBS. These results also show that the smaller the volume of deposited blood of the differing hematocrit level blood samples, the greater the variation between the front side and backside "diameters."

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the end-user's computing device (such as, a computer), partly on the end-user's computing device, as a stand-alone software package, partly on the end-user's computing device and partly on a remote computing device or entirely on the remote computing device or server. In the latter scenario, the remote computing device may be connected to the end-user's computing device through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computing device (such as, a computer), special purpose computing device, or other programmable data processing apparatus to produce a machine, such that the instructions, which execute via the processor of the computing device or other programmable data processing apparatus, create means for implementing the functions/acts specified in the flowchart and/or block diagram block or blocks. These computer program instructions may also be stored in a computer readable medium that can direct a computing device, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computing device (such as, a computer), other programmable apparatus or other devices to produce a computer implemented process such that the instructions which execute on the computer or other programmable apparatus provide processes for implementing the functions/acts specified in the flowchart and/or block diagram block or blocks.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. An apparatus for processing a specimen collection slide comprising:

a slide transport component for receiving and holding a sample slide containing an absorbed specimen;

a first imaging station having a first lighting assembly and a first camera that images a first surface of the sample slide, the first camera is adjacent to and directed at the first surface of the sample slide and the first lighting assembly is directed at an opposite second surface of the sample slide for capturing the first surface image;

a second imaging station having a second lighting assembly and a second camera that images the second surface of the sample slide, the second camera is adjacent to and directed at the second surface of the sample slide and the second lighting assembly is directed at the first surface of the sample slide for capturing the second surface image;

a computing device within said apparatus that receives imaging data from said first and second imaging stations, said computing device having a set of instructions that analyzes said imaging data and identifies a location of said absorbed specimen for removal; and a punch for removing the identified location of the absorbed specimen on the sample slide.

2. The apparatus of claim 1 wherein the first surface is the front side of the sample slide and the second surface is the backside of the sample slide.

3. The apparatus of claim 1 wherein the first surface is the backside of the sample slide and the second surface is the front side of the sample slide.

4. The apparatus of claim 1 wherein the sample slide comprises a dried blood spot specimen slide.

5. A method of processing a specimen collection slide comprising:

providing a sample slide containing a specimen absorbed through a thickness thereof;

transporting the sample slide into a processing tool having first and second imaging stations;

imaging a first surface of the sample slide by providing the sample slide in the first imaging station whereby a first lighting assembly illuminates a second surface of the sample slide while a first camera captures a first image of the absorbed specimen on the first surface of the sample slide;

imaging a second surface of the sample slide by providing the sample slide in the second imaging station whereby a second lighting assembly illuminates the first surface of the sample slide while a second camera captures a second image of the absorbed specimen on the second surface of the sample slide;

transmitting data of said first and second captured images to a computing device having a set of instructions;

using the set of instructions, analyzing said data of the first and second captured images to determine and identify a location of said absorbed specimen for removal; and removing said identified location of the absorbed specimen on the sample slide for subsequent processing.

6. The method of claim 5 wherein the first surface is the front side of the sample slide and the second surface is the backside of the sample slide.

7. The method of claim 5 wherein the first surface is the backside of the sample slide and the second surface is the front side of the sample slide.

8. The method of claim 5 wherein the first and second lighting assemblies are independently operable and adjustable for capturing various parameters of said absorbed specimen.

9. The method of claim 8 wherein the various parameters of said absorbed specimen are selected from the group consisting of gain, color, hue, brilliance and combinations thereof.

10. The method of claim 5 wherein the first and second images are captured sequentially.

11. The method of claim 5 wherein the first and second images are captured simultaneously.

12. The method of claim 5 wherein the sample slide comprises a dried blood spot specimen slide.

13. The method of claim 12 further including determining hematocrit level data of said dried blood spot using the data of the first and second captured images.

14. The method of claim 13 wherein said hematocrit levels data include color data.

15. The method of claim 13 wherein said hematocrit levels data include viscosity data.

16. The method of claim 5 further including analyzing and comparing the first image of the absorbed specimen on the first surface against the second image of the absorbed specimen on the second surface to determine a flow pattern of the absorbed specimen through the sample slide.

17. The method of claim 16 wherein a saturation volume area is calculated using at least the differential between the first image and the second image in combination with a thickness measurement of the sample slide.

18. The method of claim 17 wherein a frustum of a cone volume area is calculated and used to determine an exact location to be punched for sample removal.

19. The method of claim 5 wherein the sample slide containing the specimen includes permanent laser markings that at least uniquely identify the specimen on said sample slide.

20. A computer system comprising:

a central processing unit (CPU), a computer readable memory, and a computer readable storage media;

first program instructions to retrieve first imaging data of a first image of a specimen on a first surface of a sample slide;

second program instructions to retrieve second imaging data of a second image of the specimen on a second surface of the sample slide; and third program instructions to analyze said first imaging data and second imaging data, alone and against each other, to determine and identify a location of said specimen on the sample slide for removal, wherein the first, second, third and fourth program instructions are all stored on the computer readable storage media for execution by the CPU via the computer readable memory.

* * * * *